(12) United States Patent
Berard et al.

(10) Patent No.: US 6,405,604 B1
(45) Date of Patent: Jun. 18, 2002

(54) METHOD AND APPARATUS FOR MEASURING OIL EFFLUENT FLOW RATES

(75) Inventors: Michel Berard, Palaiseau; Gerard Segeral, Gif sur Yvette, both of (FR)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 09/486,665

(22) PCT Filed: Aug. 18, 1998

(86) PCT No.: PCT/EP98/05239

§ 371 (c)(1),
(2), (4) Date: Mar. 27, 2000

(87) PCT Pub. No.: WO99/10712

PCT Pub. Date: Mar. 4, 1999

(30) Foreign Application Priority Data

Aug. 26, 1997  (FR) .............................. 97 10648

(51) Int. Cl.[7] .............................. G01F 1/44; G01F 1/74
(52) U.S. Cl. .................................. 73/861.63; 73/861.04
(58) Field of Search ....................... 73/861.04, 861.08, 73/861.18, 861.52, 861.61, 861.63

(56) References Cited

U.S. PATENT DOCUMENTS

| 4,788,852 | A |   | 12/1988 | Martin et al. ............. 73/61.1 R |
| 4,813,270 | A | * | 3/1989 | Baillie ...................... 73/861.04 |
| 5,148,405 | A | * | 9/1992 | Belchamber et al. .... 73/861.18 |
| 5,224,372 | A | * | 7/1993 | Kolpak ...................... 73/19.03 |
| 5,349,195 | A |   | 9/1994 | Dumont ....................... 250/395 |
| 5,361,632 | A |   | 11/1994 | Magnani ....................... 73/153 |
| 5,591,922 | A | * | 1/1997 | Segeral et al. ........... 73/861.04 |
| 5,854,820 | A | * | 12/1998 | Slijkerman et al. ........... 378/51 |

FOREIGN PATENT DOCUMENTS

| EP | 0 225 741 | 6/1987 | ............. G01F/1/74 |
| EP | 0 234747 | 9/1987 | ............. G01F/1/74 |
| FR | 78 04386 | 10/1978 | ............. G01F/1/34 |
| FR | 96 14292 | 5/1998 | ............. G01N/1/20 |
| GB | 2 128 756 | 5/1984 | ............. G01F/1/00 |
| GB | 2 219 396 | 12/1989 | ............. G01P/5/22 |
| WO | 90/13859 | 11/1990 | ........... G05D/11/00 |
| WO | 93/24811 | 12/1993 | ............. G01F/1/74 |

OTHER PUBLICATIONS

Williams, J. Status of Multiphase Flow Measurement Research. SPE Publication No. 28515 (SPE Annual Tech. Conf., New Orleans, Sep. 25–28, 1994).

* cited by examiner

Primary Examiner—Max Noori
(74) Attorney, Agent, or Firm—William B. Batzer

(57) ABSTRACT

The invention relates to a flow rate measurement method adapted to oil effluents made up of multiphase fluid mixtures comprising water, oil, and gas. The effluent is passed through a Venturi in which the effluent is subjected to a pressure drop ($\Delta p$), a mean value ($<\Delta p>$) of the pressure drop is determined over a period $t_1$ corresponding to a frequency $f_1$ that is low relative to the frequency at which gas and liquid alternate in a slug flow regime, a mean value ($<\rho_m>$) is determined for the density of the fluid mixture at the constriction of the Venturi over said period $t_1$, and a total mass flow rate value $<Q>$ is deduced for the period $t_1$ under consideration from the mean values of pressure drop and of density.

54 Claims, 2 Drawing Sheets

METHOD AND APPARATUS FOR MEASURING OIL EFFLUENT FLOW RATES

Figure 1:
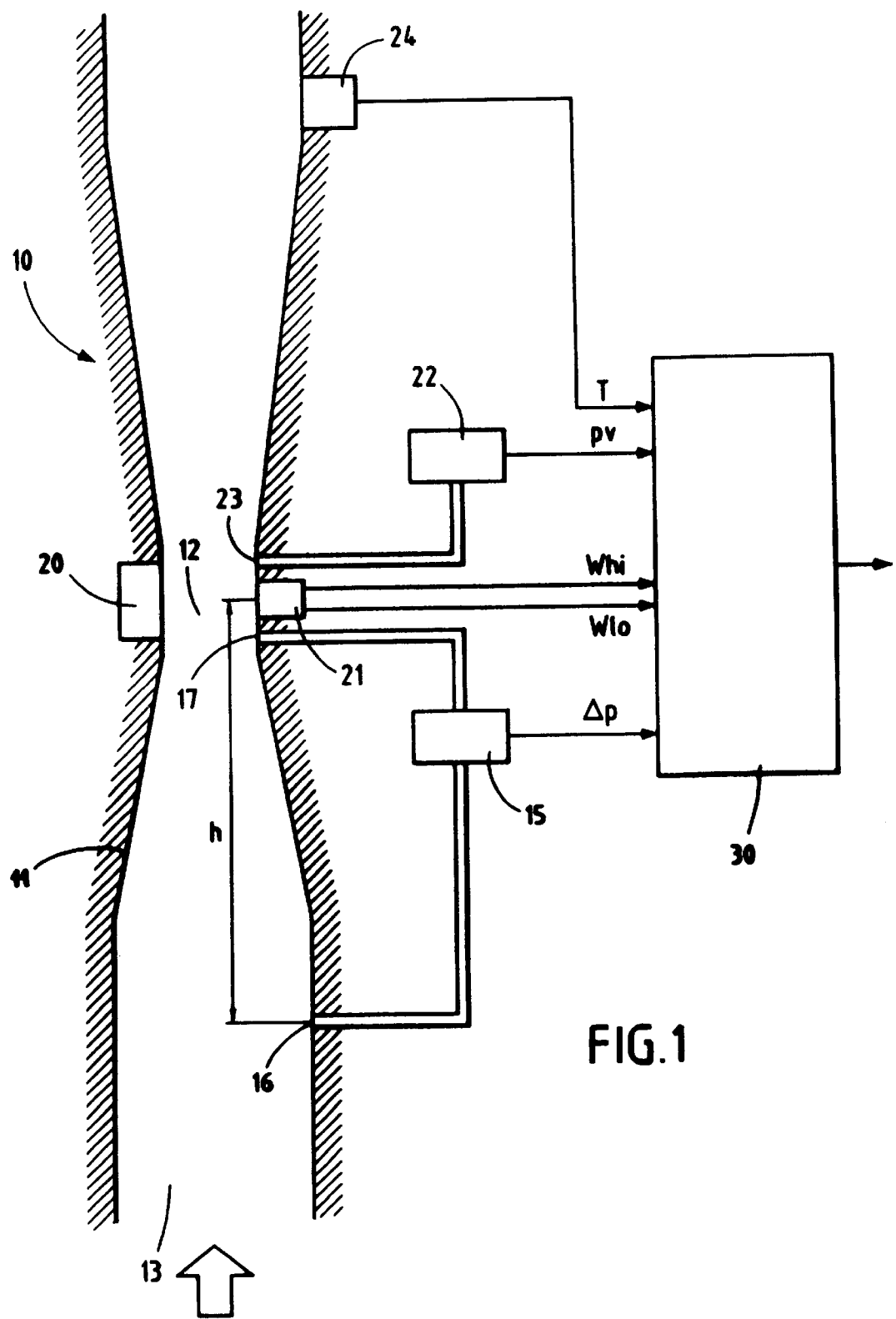

The invention relates in general to measurements intended to determine at least one characteristic of oil well effluents made up of multiphase fluids, typically comprising three phases: two liquid phases—crude oil and water—and one gas phase based on hydrocarbons. The characteristics in question are specifically the proportions of the component phases, including the water content of the liquid phase, and the flow rate values—total flow rate and the flow rates of the various phases.

The ability of the oil industry to optimize production of a reservoir relies on the possibility of evaluating the well effluent at regular intervals, in terms of quantity (flow rate) and of composition (the proportions of the various phases). This makes it possible to determine what corrective action may need to be taken. However, measuring the flow rate of oil well effluent is a problem that is complex because of the way effluents are usually made up of three phases, and because of the changes in flow conditions to which they are subject (pressure, temperature, shape of pipes). These factors give rise to a wide variety of flow regimes being observed, including some regimes of highly non-uniform and unstable character, with the proportions of the phases in the fluid mixture being capable of varying very considerably both in the flow direction (i.e. over time) and across the flow direction, in the form of phase stratification across the flow section. One extreme, but very common, case is slug flow i.e. that of a high gas content with the flow being made up of an alternation of portions that are essentially gas, known as "pockets", and portions that are constituted essentially by liquid, known as "plugs".

In the oil industry, the traditional practice is to separate the effluent into its component phases and to perform measurements on the phases separated in this way. However that technique requires separators to be installed on site, where separators are bulky and expensive items of equipment, and while wells are being tested, it also requires additional pipes to be put into place.

Numerous proposals have been put forward for developing techniques that would make it possible to avoid using such separators. A description of these developments is to be found in SPE publication 28515 (SPE Annual Technical Conference, New Orleans, Sep. 25–28, 1994) by J. Williars, "Status of multiphase flow measurement research".

Most of the propositions suggest firstly a total flow rate sensor and secondly sensors for measuring the proportions of the phases in the mixture.

Amongst those proposals, U.S. Pat. No. 4,788,852 describes apparatus comprising a Venturi and a device for measuring gamma ray attenuation at three different energy levels, the device being situated at the constriction of the Venturi.

British patent application 2 128 756 explains that it is necessary to determine two of the following three magnitudes: total mass flow rate, total volume flow rate, and mean density of the fluid. In order to compensate for non-uniformities in the flow, which give rise in particular to differences of speed between the gas and the liquid phase, thereby making any flow rate measurement difficult, and also making density measurements inaccurate, it proposes homogenizing the fluid upstream from the sensors by means of an appropriate device. In addition to improving the quality of mean density measurement, homogenization has the effect of equalizing the speeds of the gas and liquid phases, and thus of enabling the gas flow rate to be measured.

An application of that principle is described in document WO 90/13859 which provides firstly a Venturi and a gamma ray density meter placed at the constriction of the Venturi, and secondly a mixer upstream from the Venturi for the purpose of homogenizing the multiphase fluid entering the Venturi. Nevertheless, the cost and the size of such apparatus may limit its commercial applications.

The invention seeks to characterize three-phase oil effluents by means that are simple and cheap, and that are applicable to a wide variety of flow regimes, and in particular to slug flow.

In one aspect, the invention provides a flow rate measurement method adapted to oil effluents made up of multiphase fluid mixtures comprising water, oil, and gas, the method comprising the following steps: the effluent is passed through a Venturi in which the effluent is subjected to a pressure drop; a mean value of the pressure drop is determined over a period $t_1$ corresponding to a frequency $f_1$ that is low relative to the frequency at which gas and liquid alternate in a slug flow regime; a mean value is determined for the density of the fluid mixture at the constriction of the Venturi over said period $t_1$; and a total mass flow rate value <Q> is deduced for the period $t_1$ under consideration from the mean values of pressure drop and of density.

Appropriately, the density of the fluid mixture is measured by gamma ray attenuation at a first energy level at a frequency $f_2$ that is high relative to said frequency of gas/liquid alternation in a slug flow regime, and the mean of the measurements obtained in this way over each period $t_1$ corresponding to the frequency $f_1$ is formed to obtain said mean density value.

Appropriately, the frequency $f_1$ is 0.1 Hz or less than 0.1 Hz, e.g. 0.01 Hz. Appropriately, the frequency $f_2$ is greater than 20 Hz, and preferably greater than 40 Hz, e.g. being equal to 45 Hz.

Figure 2:
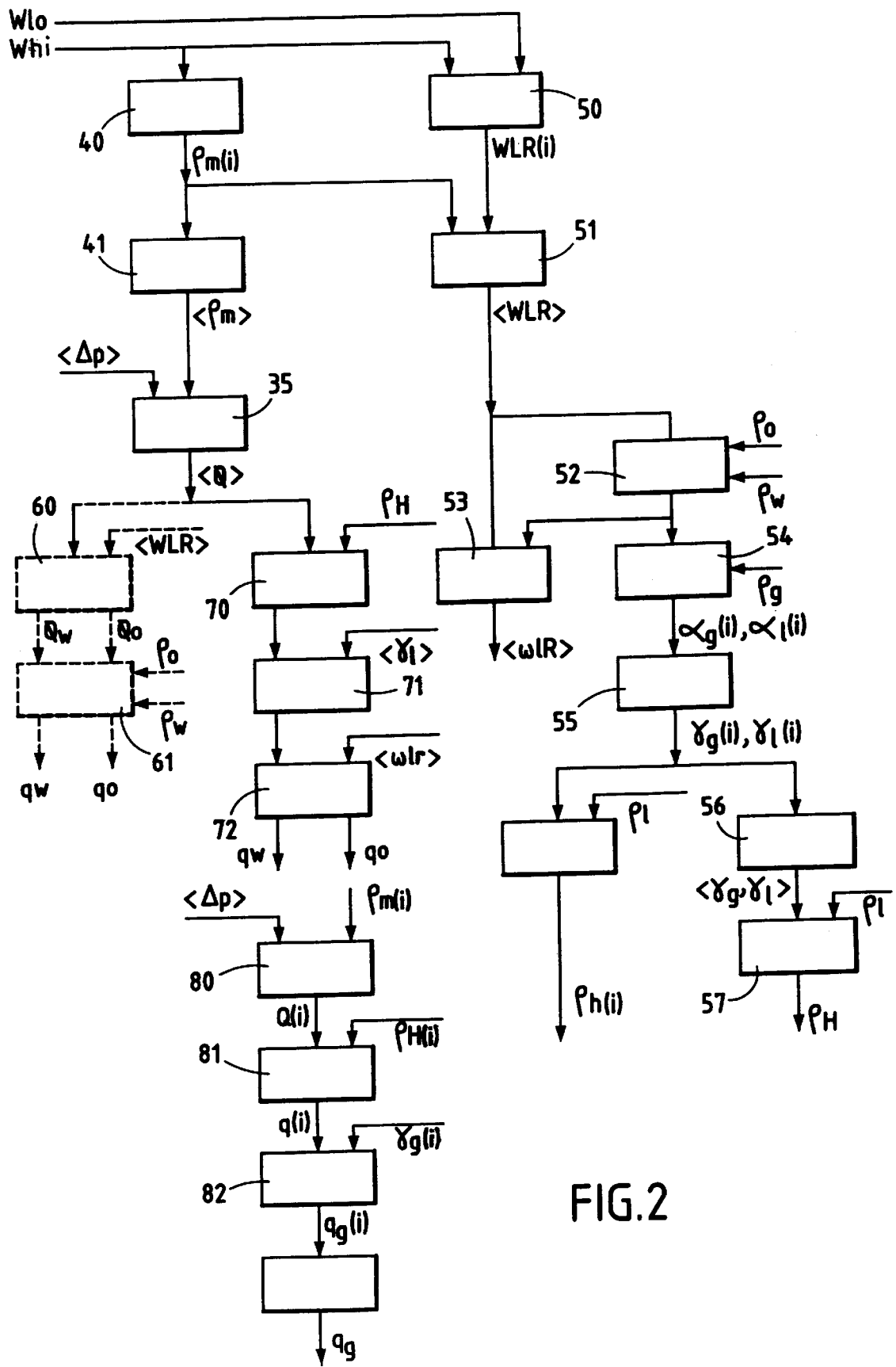

The invention will be well understood on reading the following description made with reference to the accompanying drawings, in which:

FIG. 1 is a diagram of flow measuring apparatus suitable for oil well effluents; and FIG. 2 is a block diagram illustrating the data processing operations performed by the apparatus of FIG. 1, in two embodiments.

Oil effluents are usually made up of a multiphase mixture of liquid oil, of gas (hydrocarbons), and of water. Below we use the following notations: the symbols Q and q designate mass flow rates and volume flow rates respectively; the symbol ρ designates density; the symbols α and γ designate the static and dynamic proportions of the various phases; and the indices o, w, g, and l refer respectively to the oil, water, gas, and liquid phases (where the liquid phase is the oil and the water taken together), while the index m designates the fluid mixture.

The device comprises a pipe section 10 comprising a convergent Venturi 11 whose narrowest portion 12 is referred to as the throat. In the example shown, the section of the pipe 10 is disposed vertically and the effluent flows upwards, as symbolized by arrow F.

The constriction of the flow section in the Venturi induces a pressure drop Δp between level 13, situated upstream from the Venturi at the inlet to the measurement section, and the throat 12. This pressure drop is associated with the total mass flow rate Q and with the density $\rho_m$ by the following equation:

$$\Delta p = \frac{K \cdot Q^2}{\rho_m} + \rho_m \cdot g \cdot h_v$$

where g is the acceleration due to gravity, $h_v$ is the distance between the upstream level 13 and the throat 12, and K is a constant associated essentially with the geometry of the Venturi, and which is given by:

$$K = \frac{1-\beta^4}{2C^2 \cdot A^2}$$

where $\beta$ is the constriction ratio of the Venturi, i.e. the ratio between the diameter of the throat and the upstream diameter of the Venturi, C is the discharge coefficient, and A is the section of the throat. The term $\rho_m \cdot g \cdot h_v$ is generally small or negligible. By writing $\Delta p^* = \Delta p - \rho_m \cdot g \cdot h_v$, equation (1) becomes:

$$Q = K(\Delta p^* \cdot \rho_m)^{1/2} \qquad (2)$$

where $k = K^{1/2}$.

In a preferred embodiment, the ratio $\rho$ is 0.5. With a pipe having a diameter of 10 cm, the diameter of the throat is 5 cm. The discharge coefficient C is about 1. This coefficient depends to a small extent and in predictable manner on the properties of the fluid. Traditionally, this corrective effect is taken into account by the Reynolds number.

The pressure drop $\Delta p$ is measured by means of a differential pressure sensor 15 connected to two pressure takeoffs 16 and 17 opening out into the measurement section respectively at the upstream level 13 and in the throat 12 of the Venturi. In a variant, the measurement may also be performed by means of two absolute pressure sensors connected to the pressure takeoffs 16 and 17, respectively.

The density $\rho_m$ of the fluid mixture is determined by means of a sensor which measures the attenuation of gamma rays, by using a source 20 and a detector 21 placed on opposite sides of the Venturi throat 12. The throat is provided with "windows" of a material that shows low absorption of photons at the energies under consideration. The source 20 produces gamma rays at two different energy levels, referred to below as the "high energy" level and as the "low energy" level. The detector 21 which comprises in conventional manner a scintillator crystal such as NaI and a photomultiplier produces two series of signals $W_{hi}$ and $W_{lo}$ referred to as count rates, representative of the numbers of photons detected per sampling period in the energy ranges bracketing the above-mentioned levels respectively.

These energy levels are such that the high energy count rate $W_{hi}$ is essentially sensitive to the density $\rho_m$ of the fluid mixture, while the low energy count rate $W_{lo}$ is also sensitive to the composition thereof, thus making it possible to determine the water content of the liquid phase.

Preferably the high energy level lies in a range 85 keV to 150 keV. For characterizing oil effluent, this energy range presents the remarkable property that the mass attenuation coefficient of gamma rays therein is substantially the same for water, for sodium chloride, and for oil, being about 0.17 $cm^2/g$. This means that based on the high energy attenuation, it is possible to determine the density $\rho_m$ of the fluid mixture without the need to perform auxiliary measurements to determine the properties of the individual phases of the fluid mixture (attenuation coefficients and densities). The attenuation measured by the detector 21 is expressed by the following equation:

$$A = D_v \cdot v_m \cdot \beta_m \qquad (3)$$

where $D_V$ is the distance travelled through the fluid, i.e. in this case the diameter of the Venturi throat, and $v_m$ is the mass attenuation coefficient of the fluid mixture.

Since the mass attenuation coefficients of water and oil in the above-indicated energy range are substantially identical, and since the contribution of the gas is negligible because of its very low density, the mass attenuation coefficient $v_m$, and thus the product $D_V \cdot v_m$ that appears in equation (3) can be considered as being substantially constant and independent of the densities $\rho_o$ and $\rho_w$ of the oil and water phases.

Under such conditions, the high energy attenuation $A_{hi}$ is a very advantageous indicator of the density $\rho_m$ of the mixture.

A material that is suitable for producing high energy gamma rays in the energy range under consideration, and low energy rays is gadolinium 153. This radioisotope has an emission line at an energy that is approximately 100 keV (in fact there are two lines around 100 keV, but they are so close together they can be treated as a single line), and that is entirely suitable for use as the high energy source. Gadolinium 153 also has an emission line at about 40 keV, which is suitable for the low energy level that is used to determine water content. This level provides good contrast between water and oil, since the attenuation coefficients at this level are significantly different, typical values being 0.228 $cm^2/g$ for oil and 0.291 $cm^2/g$ for sea water.

FIG. 1 also shows a pressure sensor 22 connected to a pressure takeoff 23 opening out into the throat 12 of the Venturi, which sensor produces signals representative of the pressure $p_v$ in the throat of the Venturi, and a temperature sensor 24 producing signals T representative of the temperature of the fluid mixture. The data $p_v$ and T is used in particular for determining gas density $\rho_g$ under the flow rate conditions and gas flow rate $q_g$ under normal conditions of pressure and temperature on the basis of the value for the flow rate under the flow rate conditions, determined in a manner described below. In this respect, it is preferable for the pressure to be measured at the throat of the Venturi. In contrast, it does not matter where temperature is measured. The information coming from the above-mentioned sensors is applied to a data processing unit 30 constituted by a computer running a program for delivering the looked-for results by performing various treatments based on the principle explained below. In the explanation, reference is made to the block diagram of FIG. 2.

1—Determining Total Mass Flow Rate

The need is to determine the total mass flow rate Q in a manner that is adapted to the particularly difficult case of the effluent flow regime being of the pocket-and-plug type, also called slug flow i.e. when the flow is in the form of alternating portions made up essentially of gas, known as "pockets", and portions made up essentially of liquid.

A mass flow rate value <Q>, referred to below as the mean mass flow rate, is determined (block 35) by applying above equation (2) to values defined as means <$\Delta p^*$> and <$\rho_m$> of the pressure drop $\Delta p$ and of the density of the mixture $\rho_m$ over a time interval $t_1$ which is long relative to the gas/liquid alternation period of a pocket-and-plug flow:

$$<Q> = k(<\Delta p^*><\rho_m>)^{1/2} \qquad (4)$$

It has been found that this method gives results that are robust and of satisfactory accuracy, contrary to what might have been expected, given that equation (2) is non-linear and equation (4) is a priori only applicable to a single-phase liquid since the values both of pressure drop $\Delta p$ and of density $\rho_m$ are subject to extremely sudden variations in a slug flow made up of pockets and plugs. Such a method of determining mass flow rate transforms a multiphase flow, even a flow that is extremely non-uniform such as slug flow, into a virtual single-phase flow, in that it makes equation (4) above, that applies to single-phase flows, applicable to multiphase flows. The method can thus be depicted as performing a "virtual homogenization".

The period of gas/liquid alternations in a slug flow can vary widely, depending on circumstances: typically it lies in the range 0.1 to 10 seconds. The duration $t_1$ over which the above-mentioned mean values are defined must be long relative to said alternation period. It is appropriate to set it at a value that is not less than the upper limit of the above-mentioned range, i.e. 10 s, which corresponds to a frequency, written $f_1$, of 0.1 Hz.

In the preferred implementation of the invention, these mean values are obtained as follows.

As explained above, the density is determined from the high energy attenuation $W_{hi}$ at a frequency $f_2$ which is high relative to the gas/liquid alternation frequency in a slug flow (block 40). Starting from values $\rho_m(i)$ respectively obtained for intervals $t_2$ corresponding to the frequency $f_2$, a mean density value $<\rho_m>$ is calculated over a duration corresponding to above-mentioned frequency $f_1$ (block 41). Such a method is adapted to the non-linear character of the equation relating the count rate $W_{hi}$ to the density $\rho_m$ of the fluid mixture. It is appropriate for the frequency $f_2$ to be at least 20 Hz, preferably at least 40 Hz, and for example 45 Hz.

Measurements are acquired at such a sampling frequency by means of a specialized electronic circuit associated with the detector 21 but not shown in FIG. 1. The circuit is implemented in accordance with the teaching of U.S. Pat. No. 5,349,195, and it need not be described in detail herein. Such a circuit provides fast and reliable processing of the pulses sensed in each energy window.

The inherent response time of the differential pressure sensor 15 is considerably slower than the time corresponding to the frequency $f_2$, for example it is about 0.5 Hz. However, to simplify implementation, differential pressure measurement samples are similarly acquired at the frequency $f_2$ (45 Hz in the example described) and the desired mean value $<\Delta p>$ is obtained by averaging the measured samples $\Delta p(i)$. The mean value $<\Delta p^*>$ used in determining the total mass flow in application of above equation (4) is obtained from the mean values $<\Delta p>$ and $<\rho m>$.

2 — Determining Water Content

The detector 21 measures attenuation of gamma rays by the fluid mixture at the two above-mentioned energy levels:

$$W_{hi}=W_{hi,0}\exp(-A_{hi,m})$$

$$W_{lo}=W_{lo,0}\exp(-A_{lo,m})$$

where A stands for attenuation and $W_{hi,0}$ and $W_{lo,0}$ are the high and low count rates in the absence of attenuation, as obtained by calibration.

As already mentioned above, the attenuation of the gamma rays by the fluid mixture is as follows:

$$A_m=D_v \cdot v_m \cdot \rho_m$$

where $D_v$ is the diameter of the throat of the Venturi and $v_m$ is the mass attenuation coefficient of the fluid mixture.

Given that the density of the gas phase is very low, it is possible to make the following approximations:

$$v_m \approx v_l$$

and $$\rho_m \approx \alpha_l \cdot \rho_l$$

where $v_l$ is the mass attenuation coefficient of the liquid (oil and water together) and $\alpha_l$ is the volume fraction of the liquid, and hence:

$$A_m \approx D_v \cdot v_l \cdot \rho_l \cdot \alpha_l$$

The mass attenuation coefficient of the liquid $v_l$ is a function of the attenuation coefficients of oil and water $v_o$ and $v_w$, and of the water/liquid mass ratio (WLR):

$$v_l = v_o + WLR(v_w - v_o)$$

The water/liquid mass ratio WLR can be determined from the high and low energy attenuations in the mixture, given the attenuations in oil and in water as determined by calibration, by using the following expression:

$$WLR=(\lambda_m-\lambda_o)/(\lambda_w-\lambda_o) \qquad (5)$$

where $\lambda_m$, $\lambda_o$, and $\lambda_w$ are the ratios of high energy attenuation over low energy attenuation for the fluid mixture, for oil, and for water, respectively:

$$\lambda m = A_{hi,m}/A_{lo,m}$$

$$\lambda o = A_{hi,o}/A_{lo,o}$$

$$\lambda w = A_{hi,w}/A_{lo,w}$$

The values of the water/liquid mass ratio WLR(i) are thus calculated for each of the sampling intervals $t_2(i)$ corresponding to the frequency $f_2$ which is equal to 45 Hz in the example described, on the basis of the measurements $W_{hi}(i)$ and $W_{lo}(i)$ acquired over the interval under consideration (block 50). Thereafter (block 51) a mean value $<WLR>$ is calculated over the interval $t_1$ corresponding to the frequency $f_1$ at which the mass flow rate Q is determined, with the values WLR(i) being weighted by respective confidence coefficients C(i).

The water ratio WLR is relative to the quantity of liquid in the fluid mixture. The measurement of WLR therefore applies to this quantity of liquid. When the gas content is high, the liquid content is small. Also attenuation is low because the density of the fluid mixture is low. Under such circumstances, the measurements relating to the proportions of water and oil in the liquid cannot be of good quality. The confidence coefficient should therefore decrease with increasing gas content.

Since the density $\rho_m$ of the fluid mixture is a sensitive indicator of its gas content, the confidence coefficient C(i) is advantageously determined as a function of the density $\rho_m$. (This choice is justified by the assumption that there is no systematic correlation between the composition of the liquid as expressed by the water fraction WLR, and the gas content as given by the density $\rho_m$ of the mixture.) Such a function can have several different forms. By way of example, the confidence coefficient may merely be equal to the density $\rho_m$. Naturally, other types of function can be envisaged. Also, the parameter used could be the variation in the density $\rho_m$ rather than the density proper, or a combination of these factors could be used.

To sum up, each value of WLR(i) is associated with a confidence coefficient C(i) determined as a function of the density $\rho_m(i)$ obtained as described above, and the mean value $<WLR>$ is a weighted mean of the values WLR(i):

$$<WLR>=(\Sigma C(i).WLR(i))/\Sigma C(i)$$

where $\Sigma$ symbolizes the sum of the values lying in the interval $t_1$ under consideration. From the mean value $<WLR>$ obtained for the mass fraction of water, it is possible to determine the density of the liquid phase $\rho_l$ and the mean value of the volume fraction of water $<wlr>$, knowing the densities $\rho_w$ and $\rho_o$ of water and oil respectively in the effluent. The density values $\rho_w$ and $\rho_o$ and the density of gas $\rho_g$ (under the flow conditions) can be obtained in various ways by auxiliary measurements that are known per se. By way of example, for the liquid phases, mention can be made of the sampling device described in French patent application 96 14292 filed on Nov. 22, 1996.

The density of the liquid phase is obtained (block 52) from the following equation:

$$1/\rho_l=<WLR>/\rho_w+(1-<WLR>)/\rho_o$$

and the mean volume fraction of water (block 53) is given by:

$$<wlr>=\rho_w/\rho_l \cdot <WLR>$$

It should be observed that the water content of the liquid phase is a characteristic of the effluent which is stable (or at any rate which varies slowly), unlike the gas content of the mixture. It is therefore appropriate to determine $\rho_l$ at the frequency $f_1$, as a function of the mean value $<WLR>$.

In addition, starting from the density of the liquid phase $\rho_l$ determined as described above, and from the density of the gas phase $\rho_g$ under flow conditions, it is possible (block 54) to determine the proportions of liquid $\alpha_l$ and of gas $\alpha_g$ at the frequency $f_2$ using the following equations:

$$\alpha_l(i)=(\rho_m(i)-\rho_g)/(\rho_l-\rho_g)$$

$$\alpha_l+\alpha_g=1$$

3—Determining the Oil and the Water Flow Rates

The gas mass flow rate $Q_g$ is negligible relative to the liquid mass flow rate because of the low density of the gas. It can therefore be assumed that the liquid mass flow rate $Q_l$ is approximately equal to the total mass flow rate Q:

$$Q_l \approx Q$$

The oil and water mass flow rates can then be determined (block 60) approximately from the following equations:

$$Q_w=<WLR>\cdot<Q>$$

and $$Q_o=<Q>-Q_w$$

The water and oil volume flow rates $q_w$ and $q_o$ are deduced from the mass flow rates $Q_w$ and $Q_o$ (block 61) given the respective densities $\rho_w$ and $\rho_o$ of water and oil in the effluent:

$$q_w=Q_w/r_w$$

and $$q_o=Q_o/\rho_o$$

The volume flow rate of the liquid $q_l$ can then be determined as the sum of the oil and water flow rates:

$$q_l=q_o+q_w$$

or equivalently:

$$q_l=Q_l/\rho_l \approx Q/\rho_l$$

The values obtained in this way are approximate since they assume that the gas flow rate is negligible. For more accurate determination, account is taken of the presence of gas, expressed by the volume fraction of the gas. Since the speed of gas is higher than that of the liquid (a phenomenon known as "slip"), it is necessary to make use not of the liquid and gas proportions $\alpha_l$ and $\alpha_g$ as deduced in the manner given above from the gamma ray attenuation measurements since those proportions are static proportions, but instead to make use of dynamic proportions $\gamma_l$ and $\gamma_g$ (with $\gamma_l+\gamma_g=1$) which take the slip phenomenon into account, which proportions are respectively lower than and greater than the static proportions $\alpha_l$ and $\alpha_g$. This is expressed by the equation:

$$\gamma_g=\alpha_g+\delta_g(\alpha_g)$$

where $\delta_g(\alpha_g)$ is the slip term and represents a positive correction.

When dealing with values at the throat of the Venturi, it has been found that the dynamic proportions can be determined as a function solely of the gas proportion $\alpha_g$ and are therefore essentially independent of flow rate. A suitable example of the empirical equation making such determination possible is of the form:

$$\gamma_g(i)=\alpha_g(i)+A(\gamma l(i))^m(1-\gamma_l(i))^n$$

where the coefficient A and the exponents m and n are determined empirically. A suitable example corresponds to the following values: A=1, m=1, n=6. This equation makes it possible by iterative computation to determine the dynamic proportion $\gamma_l$ from the static proportion $\alpha_l$ (block 55).

Using the values of $\gamma_l(i)$ as determined at the high frequency $f_2$ (45 Hz in this example), a mean value $<\gamma_l>$ is calculated (block 56) over each interval $t_1$ (i.e. 10 s in the example described) corresponding to the frequency $f_1$.

The liquid volume flow rate $q_l$ can then be obtained at frequency $f_1$ from the total mass flow rate $<Q>$. The total volume flow rate, taking account of slip, is given (block 70) by the following equation:

$$q=Q/\rho_H$$

where the magnitude $\rho_H$ is a value for the density of the mixture, known as the "homogeneous density", that takes account of the slip phenomenon, and that is obtained (block 57) from the equation:

$$\rho_H=<\gamma_l>\rho_l+<\gamma_g>\rho_g$$

and the liquid flow rate $q_l$ is given (block 71) by:

$$q_l=q\gamma_l$$

From which the water and oil flow rates are deduced (block 72):

$$q_w=<wlr>q_l$$

$$q_o=(1-<wlr>)q_l$$

4—Determining Gas Flow Rate

To determine the gas flow rate, a suitable method, different from that described above, relies on an "instantaneous"

value for the total mass flow rate Q(i) calculated (block 80) for each sample corresponding to the high frequency $f_2$ (45 Hz in the example described) in application of the following equation:

$$Q(i)=k[(<\Delta p>-\rho_m(i)\cdot g\cdot h_v)\cdot \rho_m(i)]^{1/2}$$

with the notation being the same as above.

An "instantaneous" value for the total volume flow rate is then deduced (block 81):

$$q(i)=Q(i)/\rho_H(i)$$

where $\rho_H(i)$ is the "homogeneous density" as defined above, determined for each sample at the high frequency $f_2$ (block 58) as follows:

$$\rho_H(i)=\gamma_l(i)\rho_l+\gamma_g(i)\rho_g$$

Based on this value for the total volume flow rate, an "instantaneous" value for the gas flow rate $q_g(i)$ is determined (block 82) for each sample at the high frequency $f_2$:

$$q_g(i)=\gamma_g(i)q(i)$$

and finally the gas flow rate $q_g$ is calculated by averaging the values $q_g(i)$ over each interval $t_1$ (10 seconds in the example described) corresponding to the low frequency $f_1$ (block 83).

What is claimed is:

1. A flow rate measurement method adapted to oil effluents made up of multiphase fluid mixtures comprising water, oil, and gas, comprising the following steps: the effluent is passed through a Venturi in which the effluent is subjected to a pressure drop ($\Delta p$); a mean value ($<\Delta p>$) of the pressure drop is determined over a period $t_1$ corresponding to a frequency $f_1$ that is low relative to the frequency at which gas and liquid alternate in a slug flow regime; a mean value ($<\rho_m>$) is determined for the density of the fluid mixture at the constriction of the Venturi over said period $t_1$; and a total mass flow rate value $<Q>$ is deduced for the period $t_1$ under consideration from the mean values of pressure drop and of density.

2. A method according to claim 1, in which the density of the fluid mixture ($\rho_m$) is measured by gamma ray attenuation at a first energy level at a frequency $f_2$ that is high relative to said frequency of gas/liquid alternation in a slug flow regime, and the mean ($<\rho_m>$) of the measurements $\rho_m(i)$ obtained in this way over each period $t_1$ corresponding to the frequency $f_1$ is formed to obtain said mean density value.

3. A method according to claim 1, in which the frequency $f_1$ is not greater than 0.1 Hz.

4. A method according to claim 2, in which the frequency $f_2$ is not less than 20 Hz.

5. A method according to claim 2, in which the attenuation of gamma rays by the fluid mixture is measured at the frequency $f_2$ at a second energy level lower than the first energy level, this measurement being performed at the constriction of the Venturi, and a value WLR(i) is deduced therefrom for the mass ratio of water relative to the liquid component of the fluid mixture.

6. A method according to claim 5, in which each of the measurements at said second energy level is associated with a confidence coefficient relating to the corresponding value $\rho_m(i)$ of the density of the fluid mixture, said coefficient being small when the density is low and higher at densities corresponding to a low proportion of gas.

7. A method according to claim 5, in which approximate values for the mass flow rate $Q_o$ and $Q_w$ and for the volume flow rates $q_o$ and $q_w$ of the oil and of the water are deduced from said total flow rate value $<Q>$ and the water ratio WLR.

8. A method according to claim 5, in which the static proportions of liquid $\alpha_l(i)$ and of gas $\alpha_g(i)$ at the frequency $f_2$ are deduced from the measurements of the fluid mixture density $\rho_m(i)$ and of the water mass ratio WLR(i) at said frequency.

9. A method according to claim 8, in which the dynamic proportions of liquid $\gamma_l(i)$ and of gas $\gamma_g(i)$ at the frequency $f_2$ are deduced from the corresponding static proportions using a determined relationship.

10. A method according to claim 9, in which, from said dynamic proportions, mean values $<\gamma_l>$ and $<\gamma_g>$ are determined over each interval $t_1$ corresponding to said frequency $f_1$.

11. A method according to claim 10, in which the total volume flow rate is deduced from the total mass flow rate $<Q>$, from said mean values $<\gamma_l>$ and $<\gamma_g>$, and from the liquid and gas densities, and the volume flow rates of oil and of water are deduced therefrom.

12. A method according to claim 9, in which total mass flow rate values Q(i) are determined at the frequency $f_2$ as a function of the corresponding density values $\rho_m(i)$, gas flow rate values $q_g(i)$ are deduced from said values Q(i), from the dynamic proportions of liquid $\gamma_l(i)$ and of gas $\gamma_g(i)$, and from the liquid and gas densities, and the mean of the values $q_g(i)$ is calculated to obtain a value for the gas flow rate over each interval $t_1$.

13. A flow rate measurement method comprising the following steps: determining a mean value ($<\Delta p>$) of the pressure drop of a fluid mixture over a period $t_1$ corresponding to a frequency $f_1$ that is low relative to the frequency at which gas and liquid alternate in a slug flow regime;

determining a mean value ($<\rho_m>$) of the density of the fluid mixture over said period $t_1$; and determining a total mass flow rate value $<Q>$ for the period $t_1$ under consideration from the mean values of pressure drop and of density.

14. The method according to claim 13, in which a density of the fluid mixture ($\rho_m(i)$) is measured by gamma ray attenuation at a frequency $f_2$ that is high relative to said frequency f1.

15. The method according to claim 14, in which the mean value ($<\rho_m>$) is determined from $\rho_m(i)$ over the period $t_1$ corresponding to the frequency $f_1$.

16. The method according to claim 13, in which the frequency $f_1$ is not greater than 0.1 Hz.

17. The method according to claim 14, in which the frequency $f_2$ is not less than 20 Hz.

18. The method according to claim 14, wherein said density of the fluid mixture $\rho_m(i)$ is measured by gamma ray attenuation at a first energy level.

19. The method according to claim 18, wherein said density of the fluid mixture is measured by gamma ray attenuation at a second energy level lower than the first energy level.

20. The method according to claim 19, wherein a value WLR(i) is deduced for the mass ratio of water relative to the liquid component of the fluid mixture.

21. The method according to claim 19, wherein each value WLR(i) is associated a confidence coefficient relating to the corresponding value $\rho_m(i)$ of the density of the fluid mixture.

22. The method according to claim 21, wherein a mean value $<WLR>$ is determined from the values WLR(i).

23. The method of claim 22, wherein said mean value $<WLR>$ is determined over a period $t_1$ corresponding to a frequency $f_1$ that is low relative to the frequency at which gas and liquid alternate in a slug flow regime.

24. The method according to claim 23, wherein approximate values for the mass flow rate $Q_o$ and $Q_w$ and for the volume flow rates $q_o$ and $q_w$ of the oil and of the water are deduced from said total flow rate value $<Q>$ and the mean value $<WLR>$.

25. The method according to claim 20, wherein static proportions of liquid $\alpha_l(i)$ and of gas $\alpha_g(i)$ at the frequency $f_2$ are deduced from the measurements of the fluid mixture density $\rho_m(i)$ and of WLR(i) at said frequency.

26. The method according to claim 25, in which dynamic proportions of liquid $\gamma_l(i)$ and of gas $\gamma_g(i)$ at the frequency $f_2$ are deduced from the corresponding static proportions.

27. The method according to claim 26, wherein mean values $<\gamma_l>$ and $<\gamma_g>$ are determined from said dynamic proportions over each interval $t_1$ corresponding to said frequency $f_1$.

28. The method according to claim 27, wherein the total volume flow rate is deduced from the total mass flow rate $<Q>$, from said mean values $<\gamma_l>$ and $<\gamma_g>$, and from the liquid and gas densities, and the volume flow rates of oil and of water are deduced therefrom.

29. The method according to claim 14, wherein total mass flow rate values Q(i) are determined at the frequency $f_2$ as a function of the corresponding density values $\rho_m(i)$.

30. The method of claim 29, wherein gas flow rate values $q_g(i)$ are deduced from said values Q(i), from the dynamic proportions of liquid $\gamma_l(i)$ and of gas $\gamma_g(i)$, and from the liquid and gas densities.

31. The method of claim 30, wherein a mean a value for the gas flow rate qg is determined over each interval $t_1$ from the values $q_g(i)$.

32. The method of claim 13, wherein said fluid mixture is passed through a Venturi.

33. An apparatus for flow rate measurement comprising:
a Venturi to receive a fluid mixture;
a pressure sensor, coupled to said Venturi, to determine a mean value ($<\Delta p>$) of a pressure drop of said fluid mixture over a period $t_1$ corresponding to a frequency $f_1$ that is low relative to the frequency at which gas and liquid alternate in a slug flow regime; and
a data processing unit, coupled to said pressure sensor and to said Venturi, to determine a mean value ($<\rho_m>$) of the density of the fluid mixture over said period $t_1$ and to determine a total mass flow rate value $<Q>$ for the period $t_1$ under consideration from the mean values of pressure drop and of density.

34. The apparatus of claim 33, further including a source of gamma rays and a detector of said gamma rays.

35. The apparatus of claim 34, wherein said source of gamma rays configured to produce gamma rays through said Venturi and said detector configured to produce a signal sensitive to a density $\rho_m$ of the fluid mixture in response to the gamma rays produced through said Venturi.

36. The apparatus of claim 35, wherein said detector coupled to said data processing unit to provide said signal.

37. The apparatus of claim 36, in which a density ($\rho_m(i)$) of the fluid mixture is measured by gamma ray attenuation at a frequency $f_2$ that is high relative to said frequency f1.

38. The apparatus of claim 37, in which the mean value ($<\rho_m>$) is determined from $\rho_m(i)$ over the period $t_1$ corresponding to the frequency $f_1$.

39. The apparatus of claim 33, in which the frequency $f_1$ is not greater than 0.1 Hz.

40. The apparatus of claim 37, in which the frequency $f_2$ is not less than 20 Hz.

41. The apparatus of claim 37, wherein said density of the fluid mixture $\rho_m(i)$ is measured by gamma ray attenuation at a first energy level.

42. The apparatus of claim 41, wherein said density of the fluid mixture is measured by gamma ray attenuation at a second energy level lower than the first energy level.

43. The apparatus of claim 42, wherein a value WLR(i) is deduced for the mass ratio of water relative to the liquid component of the fluid mixture.

44. The method according to claim 37, wherein each value WLR(i) is associated a confidence coefficient relating to the corresponding value $\rho_m(i)$ of the density of the fluid mixture.

45. The apparatus of claim 44, wherein a mean value $<WLR>$ is determined from the values WLR(i).

46. The apparatus of claim 45, wherein said mean value $<WLR>$ is determined over a period $t_1$ corresponding to a frequency $f_1$ that is low relative to the frequency at which gas and liquid alternate in a slug flow regime.

47. The apparatus of claim 46, wherein approximate values for the mass flow rate $Q_o$ and $Q_w$ and for the volume flow rates $q_o$ and $q_w$ of the oil and of the water are deduced from said total flow rate value $<Q>$ and the mean value $<WLR>$.

48. The apparatus of claim 47, wherein static proportions of liquid $\alpha_l(i)$ and of gas $\alpha_g(i)$ at the frequency $f_2$ are deduced from the measurements of the fluid mixture density $\rho_m(i)$ and of WLR(i) at said frequency.

49. The apparatus of claim 48, in which dynamic proportions of liquid $\gamma_l(i)$ and of gas $\gamma_g(i)$ at the frequency $f_2$ are deduced from the corresponding static proportions.

50. The apparatus of claim 49, wherein mean values $<\gamma_l>$ and $<\gamma_g>$ are determined from said dynamic proportions over each interval $t_1$ corresponding to said frequency $f_1$.

51. The apparatus of claim 50, wherein the total volume flow rate is deduced from the total mass flow rate $<Q>$, from said mean values $<\gamma_l>$ and $<\gamma_g>$, and from the liquid and gas densities, and the volume flow rates of oil and of water are deduced therefrom.

52. The apparatus of claim 37, wherein total mass flow rate values Q(i) are determined at the frequency $f_2$ as a function of the corresponding density values $\rho_m(i)$.

53. The apparatus of claim 52, wherein gas flow rate values $q_g(i)$ are deduced from said values Q(i), from the dynamic proportions of liquid $\gamma_l(i)$ and of gas $\gamma_g(i)$, and from the liquid and gas densities.

54. The apparatus of claim 53, wherein a mean a value for the gas flow rate qg is determined over each interval $t_1$ from the values $q_g(i)$.

* * * * *